United States Patent
Takahashi et al.

(10) Patent No.: US 7,909,462 B2
(45) Date of Patent: Mar. 22, 2011

(54) OPHTHALMOLOGIC APPARATUS

(75) Inventors: Yoshitsugu Takahashi, Tokyo (JP); Ryousuke Ito, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 108 days.

(21) Appl. No.: 12/318,115

(22) Filed: Dec. 22, 2008

(65) Prior Publication Data

US 2009/0168021 A1    Jul. 2, 2009

(30) Foreign Application Priority Data

Dec. 25, 2007 (JP) ................. 2007-332060

(51) Int. Cl.
*A61B 3/14* (2006.01)
*A61B 3/00* (2006.01)
(52) U.S. Cl. ........................ 351/208; 351/245
(58) Field of Classification Search .............. 351/245, 351/208, 211
See application file for complete search history.

(56) References Cited

U.S. PATENT DOCUMENTS

| 6,022,108 | A  | * | 2/2000 | Yoshida et al. | ........ | 351/208 |
| 2004/0189936 | A1 | * | 9/2004 | Mimura et al. | ........ | 351/205 |

FOREIGN PATENT DOCUMENTS

| JP | 2001-187024 | * | 7/2001 |
| JP | 3610133 | | 1/2005 |
| JP | 3628084 | | 3/2005 |
| JP | 2007-282671 | | 11/2007 |
| JP | 2007-282672 | | 11/2007 |

OTHER PUBLICATIONS

European Search Report dated Mar. 30, 2009, issued on the corresponding European patent application No. 08 02 2377.9.

* cited by examiner

*Primary Examiner* — Jordan M. Schwartz
(74) *Attorney, Agent, or Firm* — Edwards Angell Palmer & Dodge LLP

(57) ABSTRACT

An opthalmologic apparatus has an examination unit including a plurality of examining parts for executing different examinations on an eye to and a driver moving the examination unit in the horizontal direction and in the anteroposterior direction. The opthalmologic apparatus controls the driver when switching a examination subject by the examination unit from one eye to the other eye to cause the examination unit to retreat by only a retreating distance according to the working distance of an examination part positioned at the examination position for the one eye. The examination unit retreats by only a distance according to the working distance. Therefore, it is possible to achieve both reductions in examination time and improvements for safety by preventing an examining part comes into contact with the patient.

8 Claims, 10 Drawing Sheets

OPHTHALMOLOGIC APPARATUS

BACKGROUND OF THE INVENTION

1. Field of the Invention

The present invention relates to an opthalmologic apparatus for executing a plurality of examinations on both the right and left eyes.

2. Description of the Related Art

Known examples of an opthalmologic apparatus for executing a plurality of examinations on each of the eyes include the apparatus disclosed in Japanese Unexamined Patent Application Publication No. 2007-282671. This opthalmologic apparatus is provided with a measuring unit including a first measuring part with a long working distance and a second measuring part with a short working distance.

These measuring parts are arranged next to each other in the vertical direction. This opthalmologic apparatus is configured to, when switching from measurement by the first measuring part to measurement by the second measuring part, move the second measuring part in a direction of the working distance.

Furthermore, the opthalmologic apparatus is configured to, when switching between the right and left eyes during the measurement by the second measuring part, move the second measuring part in the direction of the working distance in the course of moving the measuring unit in the horizontal direction. According to such a conventional opthalmologic apparatus, it is possible to prevent the apparatus from coming into contact with a unit for supporting the face or head of a patient.

Such an opthalmologic apparatus needs a time of at least several seconds to switch between the right and left eyes. Furthermore, when executing a plurality of examinations on each of the eyes, the apparatus may need two or more switching operations. For these reasons, there is a problem that an examination time becomes longer and load on the subject becomes more. In particular, actual measurement of eye refractive power, ocular tension, etc., is completed in a short time, but the operation of switching between the right and left eyes takes significantly more time than a time for the actual measurement. Therefore, the latter time reduction has a great effect on reduction of the overall examination time.

It is also possible to adjust the measuring unit to move at a high speed in order to reduce the time required for switching between the right and left eyes. However, in consideration of the weight of the measuring unit, etc., the safety for the subject may be deteriorated in the event of poor accuracy of the moving operation of the measuring unit, and there is also the risk of making the subject feel anxious or surprised due to the sound generated during the movement.

SUMMARY OF THE INVENTION

The present invention has been designed in order to solve the above problems and to provide an opthalmologic apparatus capable of reducing an examination time while securing the safety for the subject.

In an aspect of the present invention, an opthalmologic apparatus has: an examination unit including a plurality of examining parts executing different examinations on an eye; a driver configured to move the examination unit in a horizontal direction and an anteroposterior direction; and a controller configured to, when an examination target by the examination unit is switched from one eye to the other eye, control the driver to make the examination unit retreat by a retreat distance corresponding to a working distance of the examining part located at an examination position for the one eye.

According to the aspect of the opthalmologic apparatus according to the present invention, since the examination unit is made to retreat by the distance corresponding to the working distance, it is not required to make it retreat by a unnecessarily long distance.

Therefore, it is possible to reduce the examination time.

Furthermore, it is also possible to increase the safety by preventing the examining part from coming into contact with the subject.

DETAILED DESCRIPTION OF THE PREFERRED EMBODIMENT

An embodiment of an opthalmologic apparatus according to the present invention will now be described.

[Configuration]

Figure 1:
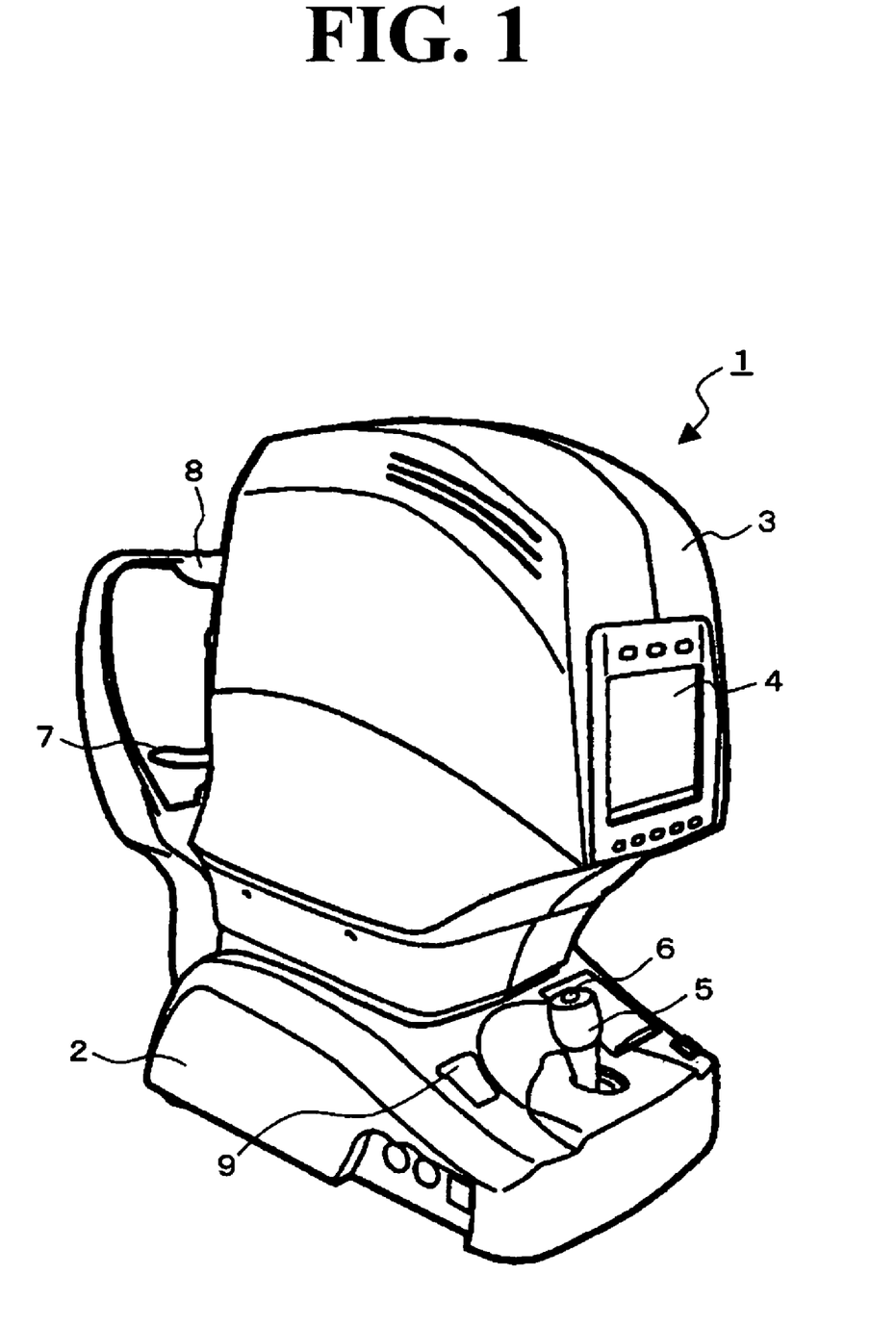
FIG. 1 shows an example of the exterior configuration of an opthalmologic apparatus according to a present embodiment.

FIGS. 1 to 6 show a configuration example of the opthalmologic apparatus according to the present embodiment. The exterior of an opthalmologic apparatus 1 is shown in FIG. 1. As conventional, the opthalmologic apparatus 1 includes a base 2, a measuring head 3, a display 4, a control lever 5, a measurement switch 6, a jaw rest 7, a forehead rest 8, a jaw-rest moving switch 9, etc.

The subject is examined with his/her jaw placed on the jaw rest 7 and his/her forehead placed in contact with the forehead rest 8. At this moment, the subject rests with his/her face toward the measuring head 3. The operator operates the jaw-rest moving switch 9 to move the jaw rest 7 vertically and adjust the position of the face of the patient.

The operator is located on a side where the display 4 and the control lever 5 are disposed, and examines an eye of the subject.

The vertical, anteroposterior and horizontal directions in the specification will be defined as described below. (1) The vertical direction is the perpendicular direction. (2) The anteroposterior direction is a direction that is orthogonal to the vertical direction and that connects the operator side and the subject side. In other words, the anteroposterior direction is a direction that is orthogonal to the vertical direction and that connects the side of the display 4 and the side of the jaw rest 7. Herein, a direction toward the patient is referred to as a forward direction, and the opposite direction is referred to as a backward direction. (3) The horizontal direction is a direction orthogonal to both the vertical direction and the anteroposterior direction. Herein, a direction from the right eye to the left eye of the patient is referred to as a leftward direction, and the opposite direction is referred to as a rightward direction.

As conventional, the base 2 houses a calculation control circuit, a storage, a power supply circuit, etc. The measuring head 3 is movable in the vertical, anteroposterior and horizontal directions, i.e., three-dimensionally with respect to the base 2. The measuring head 3 is moved by a drive mechanism 10, which will be described later. The measuring head 3 is moved by the drive mechanism 10 when the alignment with respect to an eye is adjusted, when an examination method is changed, when an examined eye is changed from one eye to the other eye, when the measuring head is advanced to a working distance appropriate for an examination method, and when the measuring head is made to retreat to a safe distance when each of the abovementioned operations is performed.

The display 4 displays an image of an eye, such as an anterior segment image. Moreover, the display 4 displays various kinds of examination information, such as patient information, examination conditions and examination results. The display 4 may be a touch panel display. In this case, various kinds of software keys are displayed in the display 4, and the operator can cause the opthalmologic apparatus 1 to execute a desired operation by pressing these software keys.

The control lever 5 is operated when, for example, the measuring head 3 is moved manually. The measurement switch 6 is operated when measurement on an eye is executed. There are switches disposed around the display 4 (above and below in FIG. 1). These switches are used at the time of alignment with respect to an eye, adjustment of the display 4, etc.

[Drive Mechanism]

Figure 2:
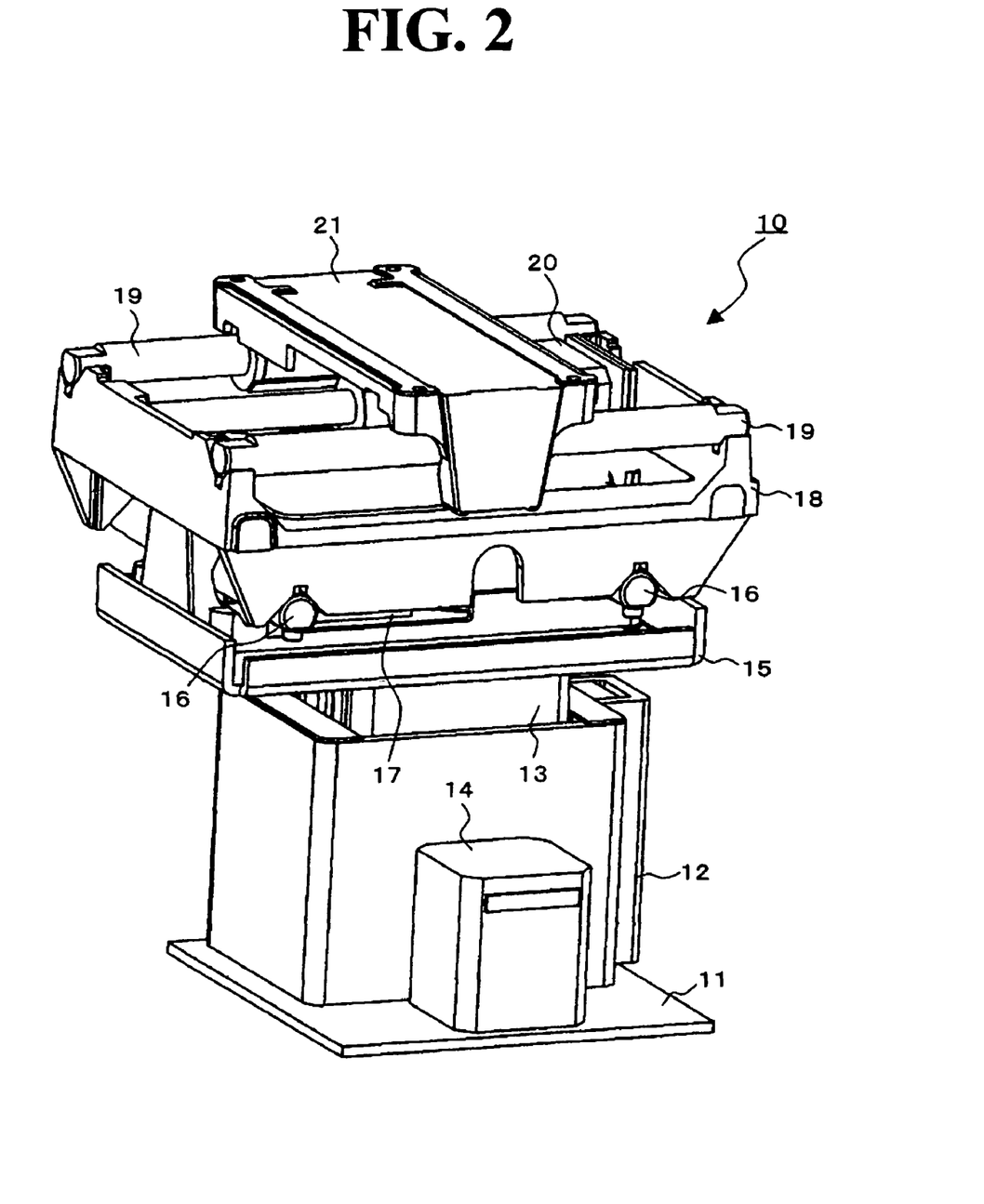
FIG. 2 shows an example of the configuration of a drive mechanism of the opthalmologic apparatus according to the present embodiment.

The drive mechanism 10 shown in FIG. 2 has a configuration for moving the measuring head 3 in the vertical, anteroposterior and horizontal directions. The drive mechanism 10 is housed in the base 2.

A bottom plate 11 is installed in a fixed state within the base 2.

A supporting part 12 is installed in a fixed state on the top face of the bottom plate 11. The supporting part 12 has a hollow part. A support column 13 is placed in the hollow part. A vertical drive motor 14 is placed in a fixed state on the top face of the bottom plate 11.

The vertical drive motor 14 includes an actuator such as a stepping motor (sometimes referred to as a pulse motor). A driving force generated by the vertical drive motor 14 is conveyed by a driving-force conveying mechanism (not illustrated) that includes gears, etc., to move the support column 13 in the vertical direction. A vertically moving stage 15 is attached in a fixed state to the upper end of the support column 13. The vertically moving stage 15 moves in the vertical direction together with the support column 13.

Near the respective ends in the horizontal direction of the top face of the vertically moving stage 15, anteroposterior rails 16 are disposed. Each of the anteroposterior rails 16 is disposed so that the longitudinal direction thereof is along the anteroposterior direction. An anteroposterior moving stage 18 is mounted on each of the anteroposterior rails 16 so as to be movable in the anteroposterior direction.

Furthermore, an anteroposterior drive motor 17 is disposed on the top face of the vertically moving stage 15. The anteroposterior drive motor 17 includes, for example, an actuator such as a stepping motor. A driving force generated by the anteroposterior drive motor 17 is conveyed by a driving-force conveying mechanism, which is not illustrated, and moves the anteroposterior moving stage 18 along the anteroposterior rail 16. Consequently, the anteroposterior moving stage 18 is moved in the anteroposterior direction with respect to the vertically moving stage 15.

Near the respective ends in the anteroposterior direction of the top face of the anteroposterior moving stage 18, horizontal rails 19 are disposed. Each of the horizontal rails 19 is disposed so that the longitudinal direction thereof is along the horizontal direction. A horizontally moving stage 21 is mounted on the horizontal rails 19 so as to be movable in the horizontal direction.

Furthermore, a horizontal drive motor 20 is disposed on the top face of the anteroposterior moving stage 18. The horizontal drive motor 20 includes, for example, an actuator such as a stepping motor.

A driving force generated by the horizontal drive motor 20 is conveyed by a driving-force conveying mechanism, which is not illustrated, and moves the horizontally moving stage 21 along the horizontal rails 19. Consequently, the horizontally moving stage 21 is moved in the horizontal direction with respect to the anteroposterior moving stage 18.

The measuring head 3 is mounted on the horizontally moving stage 21. According to the drive mechanism 10, it is possible to move the measuring head 3 in the vertical direction, anteroposterior direction and horizontal direction separately.

[Measuring Head]

The measuring head 3 is provided with a plurality of examining parts configured to execute different opthalmologic examinations on an eye, and is equivalent to an example of an "examination unit" of the present invention. In this embodiment, an eye-refractive-power examination, a tonometry and a corneal-thickness examination are employed as opthalmologic examinations. Opthalmologic examinations that can be executed by the opthalmologic apparatus according to the present invention are not limited to the above, and may include any examinations (measurement or photography) as exemplified below: visual acuity test, corneal-curvature examination, color-vision examination, visual-field examination, anterior-segment photography, corneal-endothelium photography, fundus-oculi photography, OCT (Optical Coherence Tomography) examination, SLO (Scanning Laser Opthalmoscope) examination, ultrasonic examination, radiation examination, etc. Moreover, the number of opthalmologic examinations that can be executed by the opthalmologic apparatus according to the present invention may be any number of two or more.

Figure 3:
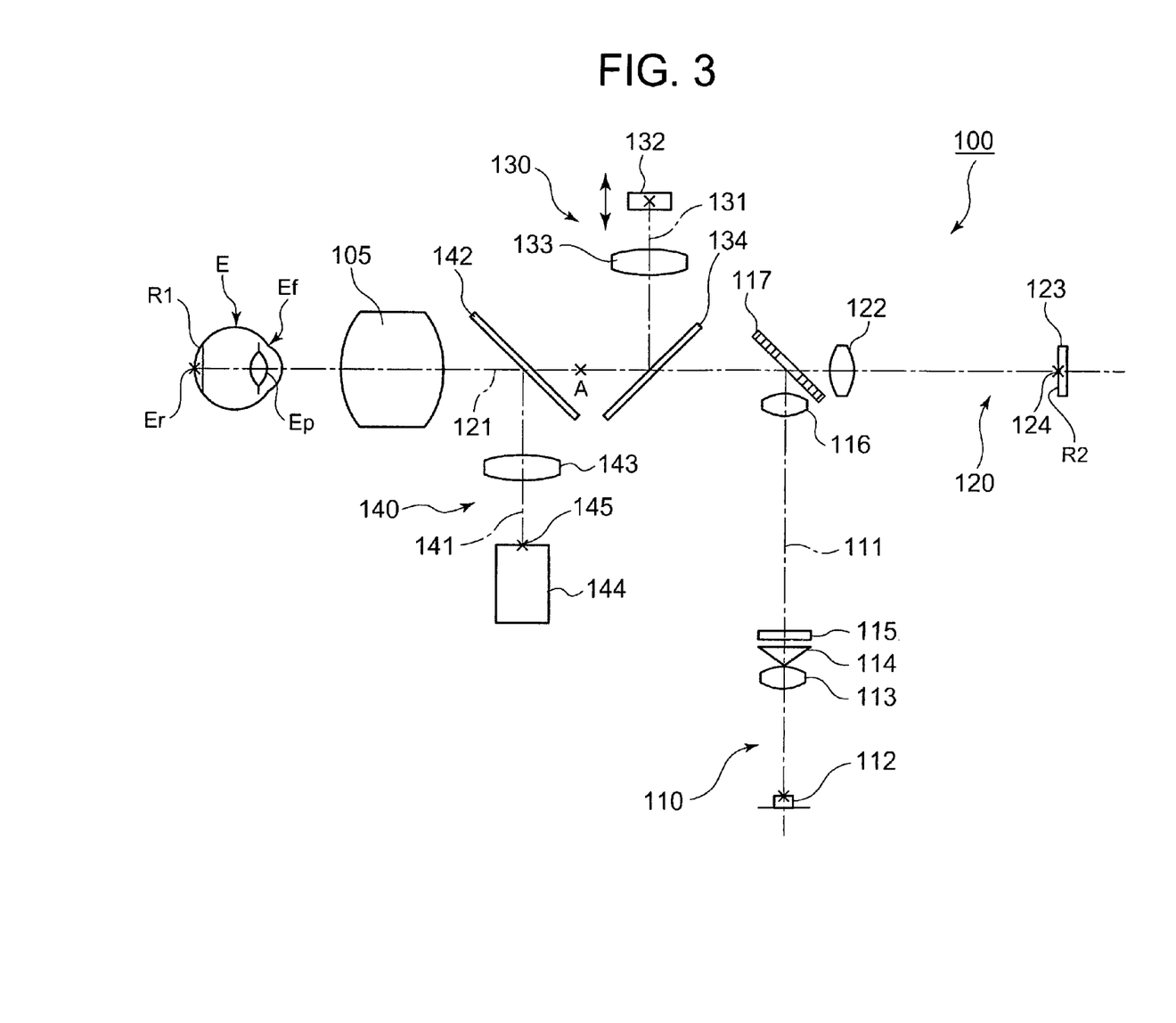
FIG. 3 shows a first configuration example of an optical system of the opthalmologic apparatus according to the present embodiment.
Figure 4:
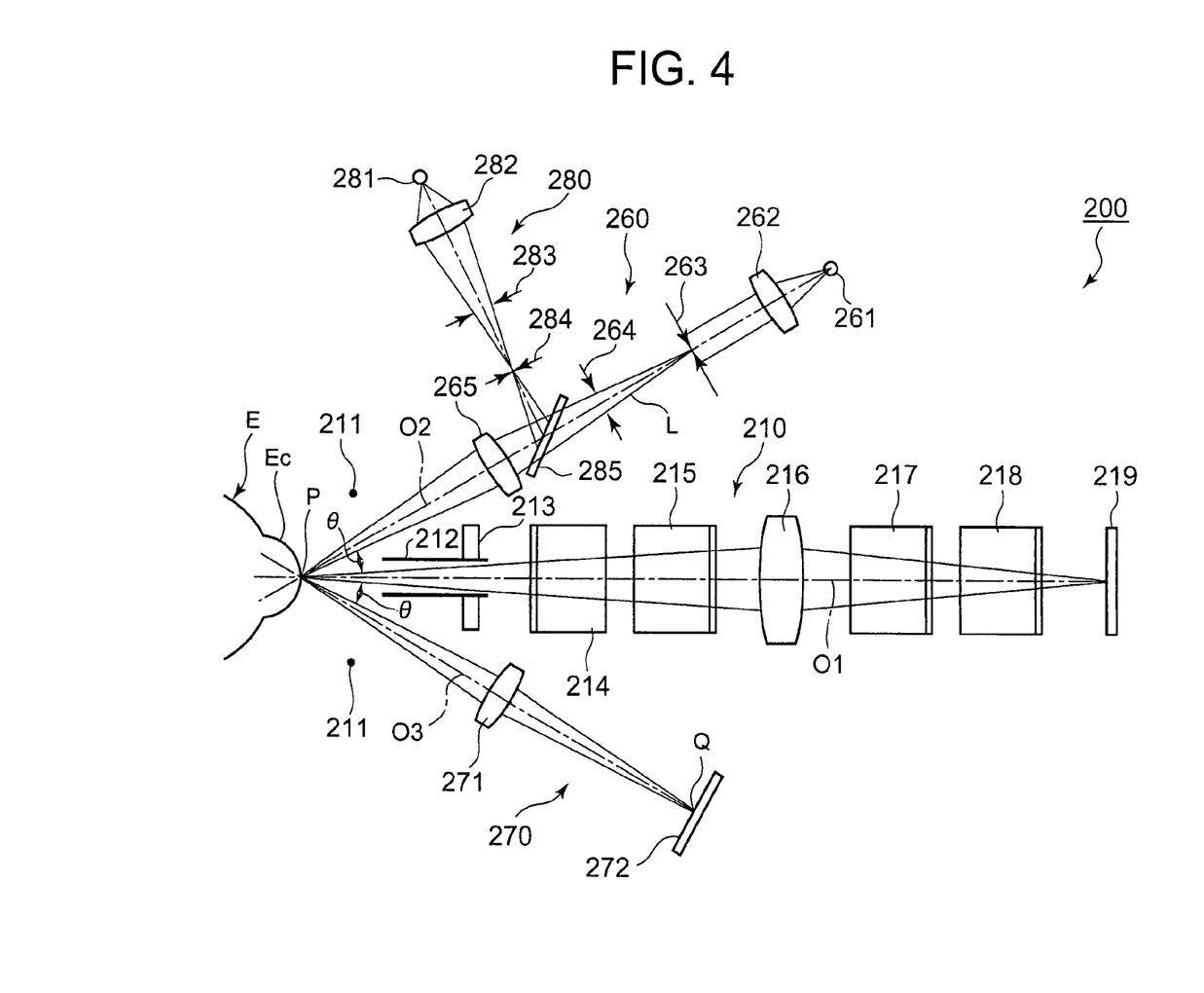
FIG. 4 shows a second configuration example of the optical system of the opthalmologic apparatus according to the present embodiment, taken from the vertical direction of the apparatus.
Figure 5:
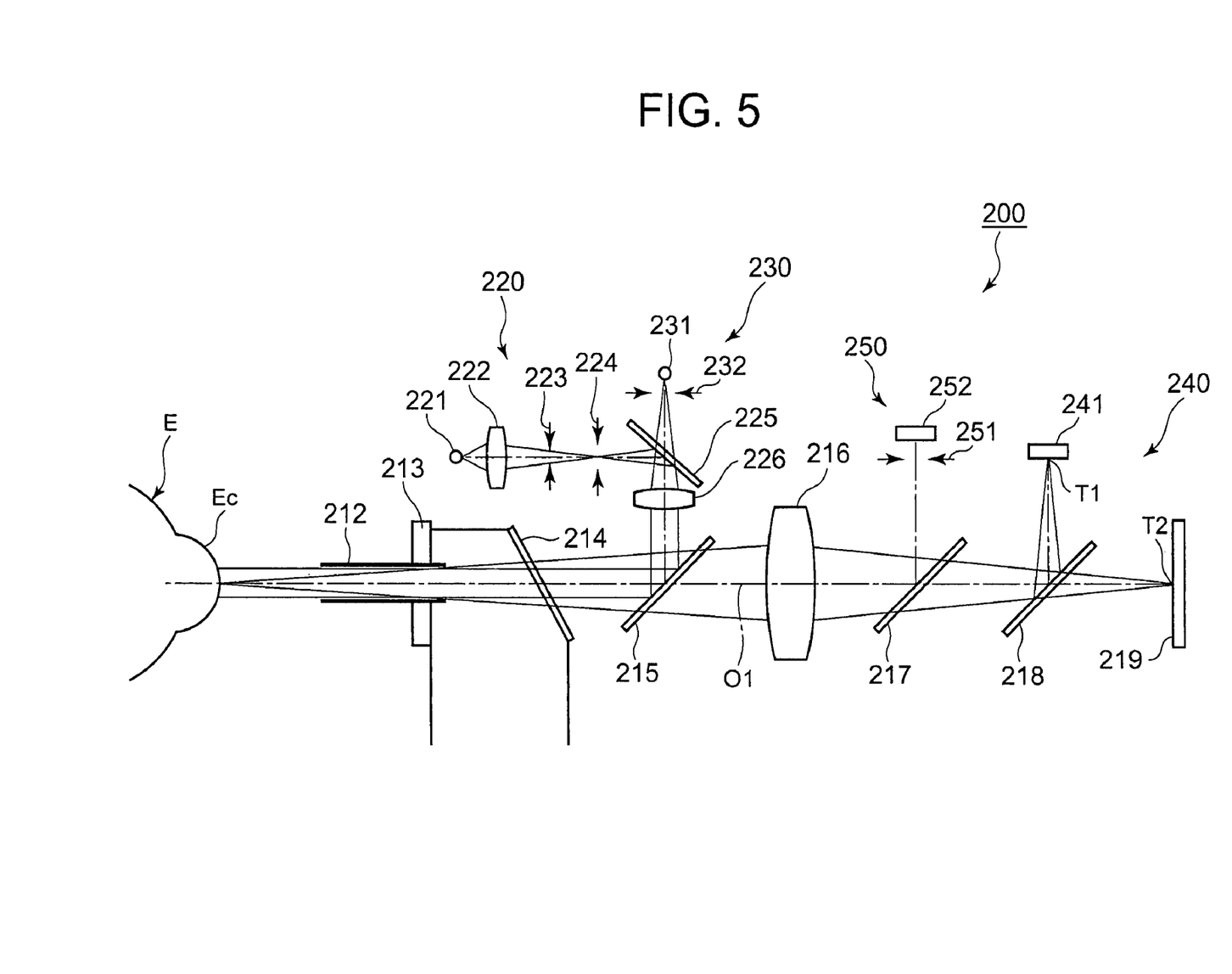
FIG. 5 shows the second configuration example of the optical system of the opthalmologic apparatus according to the present embodiment, taken from the horizontal direction of the apparatus.

The configuration of an optical system housed in the measuring head 3 is shown in FIGS. 3 to 5. An eye-refractive-power measuring system 100 shown in FIG. 3 is an optical system for measuring the eye refractive power of an eye E (the sphericity, degree of astigmatism, astigmatic axis angle, etc.).

A tonometry system 200 shown in FIGS. 4 and 5 is an optical system for measuring the ocular tension of the eye E.

The tonometry system 200 is also used for measuring the corneal thickness of the eye E. The respective measuring systems 100 and 200 are each provided with a mechanism for driving a member, an electric circuit, etc., other than the illustrated members such as an optical element.

The eye-refractive-power measuring system 100 and the tonometry system 200 are, for example, housed in separate cases (not illustrated). The eye-refractive-power measuring system 100 and the tonometry system 200 are arranged, for example, next to each other in the vertical direction. In the present embodiment, the eye-refractive-power measuring system 100 is placed above, and the tonometry system 200 is placed below.

{Eye-Refractive-Power Measuring System}

As shown in FIG. 3, the eye-refractive-power measuring system 100 has a configuration similar to that of a conventional eye-refractive-power measuring apparatus (auto refractometer) (refer to, for example, Japanese Patent Publication No. 2937373). The eye-refractive-power measuring system 100 includes an objective lens 105, a projecting system 110, an image-forming system 120, a fixation-target projecting system 130, and an anterior-segment observing system 140.

The projecting system 110 includes an infrared LED (Light Emitting Diode) 112, a relay lens 113, a conic prism 114, a ring-shaped aperture diaphragm 115, and a relay lens 116, which are arranged along a reflection light axis 111 of an aperture mirror 117. The infrared LED 112 and the aperture mirror 117 are placed so as to be conjugated with respect to the relay lenses 113 and 116. The aperture mirror 117 and a pupil Ep of the eye E are placed so as to be conjugated with respect to the objective lens 105. Furthermore, the conic prism 114 and a fundus oculi Er are placed so as to be conjugated with respect to the relay lens 116 and the objective lens 105.

The image-forming system 120 includes optical elements disposed along an optical axis 121. A relay lens 122 and a CCD image sensor 123 are disposed on the optical axis 121 behind the aperture mirror 117. Assuming a conjugated position to the fundus oculi Er with respect to the objective lens 105 is A, the position A and a light-receiving face 124 of the CCD image sensor 123 are conjugated with respect to the relay lens 122.

The fixation-target projecting system 130 includes a fixation-target presenting part 132, a relay lens 133 and a dichroic mirror 134, which are arranged along an optical axis 131 branched out from a position on the optical axis 121 between the position A and the aperture mirror 117. The dichroic mirror 134, which is obliquely disposed on the optical axis 121, transmits an infrared light and reflects a visible light. The fixation-target presenting part 132 is movable along the optical axis 131. The fixation-target presenting part 132 is placed at a position conjugated to the position A with respect to the relay lens 133.

The anterior-segment observing system 140 includes a half mirror 142, a relay lens 143 and an imaging device 144, which are arranged along an optical axis 141 branched out from a position on the optical axis 121 between the objective lens 105 and the position A. The half mirror 142 is obliquely disposed on the optical axis 121. The imaging device 144 includes a solid-state imaging element, such as a CCD image sensor and a CMOS image sensor, an imaging tube or the like. A light-receiving face 145 of the imaging device 144 is placed so as to be conjugated to the anterior segment Ef with respect to the objective lens 105 and the relay lens 143.

A mode of measuring eye refractive power by using the eye-refractive-power measuring system 100 will now be described. Here, it is assumed that the alignment of the eye-refractive-power measuring system 100 with respect to the eye E is completed. During measurement, an image of the anterior segment Ef is acquired by the anterior-segment observing system 140. This image is displayed in the display 4, whereby it is possible to check if the anterior segment Ef is located in an appropriate position. Furthermore, a fixation target is projected to the fundus oculi Er by the fixation-target projecting system 130, whereby an eye is fixated in a foggy state.

In this state, the infrared LED 112 is lit to form a ring image R1 on the fundus oculi Er. The reflected light of the ring image R1 from the fundus oculi Er is projected to the light-receiving face 124 of the CCD image sensor 123. The CCD image sensor 123 detects the projected image (ring image R2). As conventional, the opthalmologic apparatus 1 (eye-refractive-power calculator 41 in FIG. 6) obtains the eye refractive power of the eye E by analyzing the shape of the ring image R2.

{Tonometry System}

As shown in FIGS. 4 and 5, the tonometry system 200 has a configuration similar to that of a conventional non-contact tonometer (refer to, for example, Japanese Unexamined Patent Application Publication No. 2002-102170). The tonometry system 200 includes an anterior-segment observing system 210, an XY alignment target projecting system 220, a fixation-target projecting system 230, an XY alignment detecting system 240, a corneal deformation detecting system 250, a slit projecting system 260, a light-receiving system 270, and a Z alignment target projecting system 280. Herein, X, Y and Z respectively represent coordinate axes of a three-dimensional coordinate system. An X direction corresponds to the horizontal direction, a Y direction corresponds to the vertical direction, and a Z direction corresponds to the anteroposterior direction.

The anterior-segment observing system 210 includes a plurality of anterior-segment illuminating sources 211, an air-puff nozzle 212, an anterior-segment window glass 213, a chamber window glass 214, a half mirror 215, an objective lens 216, half mirrors 217 and 218, and a CCD image sensor 219. The members 212 to 219 other than the anterior-segment illuminating light sources 211 are arranged on an optical axis O1. The air-puff nozzle 212 blows air puff generated by an air compression mechanism, which is not shown, toward the eye E.

The plurality of anterior-segment illuminating light sources 211 are arranged at the horizontal positions of the eye E, and directly illuminate the anterior segment. The illuminating light emitted from the anterior-segment illuminating light source 211 is reflected by the anterior segment of the eye E, passes through the air-puff nozzle 212, passes through the anterior-segment window glass 213, the chamber window glass 214 and the half mirror 215, and is converged by the objective lens 216. The converged light flux passes through the half mirrors 217 and 218 and is projected on the light-receiving face of the CCD image sensor 219. The CCD image sensor 219 detects the projected image to photograph the anterior segment of the eye E.

The XY alignment target projecting system 220 includes an alignment light source 221, a converging lens 222, an aperture diaphragm 223, a pinhole plate 224, a dichroic mirror 225, and a projection lens 226. These members 221 to 226 are arranged on an optical axis branched out from the optical axis O1 by the half mirror 215. The dichroic mirror 225 reflects an infrared light and transmits a visible light.

The alignment light source 221 outputs an infrared light. The infrared light is converged by the converging lens 222 to pass through the aperture diaphragm 223 and is guided to the pinhole plate 224. The light flux passed through the pinhole plate 224 is reflected by the dichroic mirror 225 and is collimated by the projection lens 226. The collimated light flux is reflected by the half mirror 215 and applied to the eye E along the optical axis O1. The applied light is used as an XY alignment target light for alignment in the XY direction.

The fixation-target projecting system 230 includes a fixation-target light source 231, a pinhole plate 232, and a projection lens 226, which are arranged on an optical axis branched out from the optical axis O1 by the half mirror 215.

The visible light outputted from the fixation-target light source 231 passes through the pinhole plate 232 and the dichroic mirror 225 and is collimated by the projection lens 226. The parallel light flux is reflected by the half mirror 215 and is projected to the fundus oculi of the eye E along the optical axis O1. The reflected light is used as a fixation target.

The XY alignment detecting system 240 includes the half mirror 218 and an optical sensor 241. The optical sensor 241 is composed of a sensor capable of detecting a position, such as a PSD (Position Sensitive Detector).

The XY alignment target light applied to the eye E by the XY alignment target projecting system 220 is reflected by (the surface of) the cornea Ec. The corneal reflection light passes through the inside of the air-puff nozzle 212, the anterior segment window glass 213, the chamber window glass 214 and the half mirror 215, and is converted into a converged light flux by the objective lens 216. The converged light flux transmitted by the half mirror 217 is split by the half mirror 218. The component reflected by the half mirror 218 forms a bright spot image T1 on the light-receiving face of the optical sensor 241. On the other hand, the component transmitted by the half mirror 218 forms a bright spot image T2 on the light-receiving face of the CCD image sensor 219.

The opthalmologic apparatus 1 (e.g., a calculator 40 in FIG. 6) calculates a misalignment in the XY direction of the tonometry system 200 with respect to the cornea Ec, based on the results of detection of the bright spot image T1 by the optical sensor 241. On the other hand, the results of detection of the bright spot image T2 by the CCD image sensor 219 are displayed on the display 4 together with the anterior segment image of the eye E. Consequently, it is possible to visually check the alignment state in the XY direction.

The light flux reflected by the half mirror 217 is guided to the corneal deformation detecting system 250 and detected by the optical sensor 252 via the pinhole plate 251. The optical sensor 252 is a sensor capable of detecting the amount of light, such as a photodiode. The optical sensor 252 detects the amount of light reflected from the cornea Ec applanated by the air puff from the air-puff nozzle 212. The opthalmologic apparatus 1 (ocular-tension calculator 42) obtains the amount of deformation of the cornea Ec from the detection result, thereby obtaining the value of ocular tension of the eye E.

The slit-projecting system 260 includes a slit light source 261, a converging lens 262, a slit 263, a rectangular aperture diaphragm 264, a half mirror 285, and a projection lens 265. These members are arranged on an optical axis O2. The slit 263 is placed so as to be conjugated to the back face of the cornea Ec with respect to the projection lens 265.

The slit light source 261 outputs an infrared light. The infrared light is converged by the converging lens 262 and guided to the slit 263. The infrared light (a slit light flux L) passed through the slit 263 passes through the rectangular aperture diaphragm 264 and the half mirror 285, and is projected to the cornea Ec by the projection lens 265.

The slit light flux L projected to the cornea Ec is reflected at the corneal front face or corneal back face.

A light-receiving system 270 includes an image-forming lens 271 and a line sensor 272. These members are arranged on an optical axis O3. The optical axes O2 and O3 are disposed so as to form an angle θ in the opposite direction of the horizontal direction with respect to the optical axis O1.

The corneal reflection light (front face reflection, back face reflection) of the slit light flux L is converged by the image-forming lens 271, thereby forming an image on the light-receiving face of the line sensor 272. The opthalmologic apparatus 1 (the calculator 40) obtains the distribution of the corneal reflection light amount based on signals outputted by the line sensor 272, and executes alignment in the Z direction based on this distribution of the light amount. Furthermore, the opthalmologic apparatus 1 (corneal-thickness calculator 43) obtains the thickness of the cornea Ec based on two peak positions of the distribution of corneal reflection light amount.

The Z alignment target projecting system 280 includes an alignment light source 281, a converging lens 282, an aperture diaphragm 283, a pinhole plate 284, a half mirror 285, and a projection lens 265. The pinhole plate 284 is placed at the focal position of the projection lens 265. The aperture diaphragm 283 is placed so as to be conjugated to a corneal apex P with respect to the projection lens 265.

The infrared light outputted from the alignment light source 281 is converged by the converging lens 282, and reaches the aperture diaphragm 283. Part of the infrared light passed through the aperture diaphragm 283 passes through the pinhole plate 284, and is reflected by the half mirror 285 and projected to the cornea Ec by the projection lens 265. The reflection light by (the surface of) the cornea Ec of the infrared light is converged by the image-forming lens 271, thereby forming a bright spot image Q on the light-receiving face of the alignment sensor 272. The results of detection of the bright spot image Q are used for the alignment (rough adjustment) in the Z direction.

[Control System]

Figure 6:
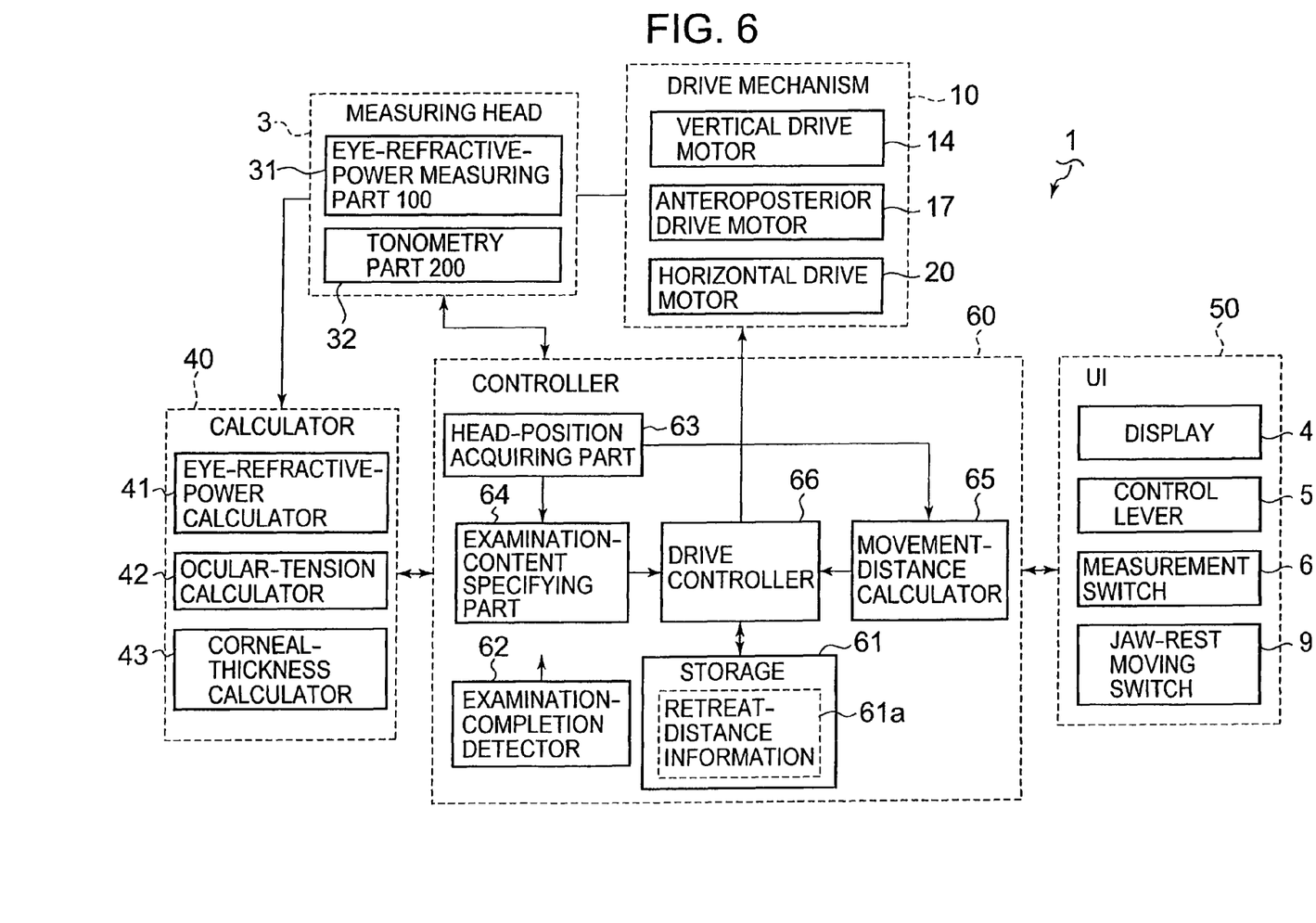
FIG. 6 shows an example of the configuration of a control system of the opthalmologic apparatus according to the present embodiment.

A configuration example of a control system of the opthalmologic apparatus 1 is shown in FIG. 6.

{Measuring Head}

The measuring head 3 has an eye-refractive-power measuring part 31 and a tonometry part 32. The eye-refractive-power measuring part 31 includes a configuration for measuring the eye refractive power of the eye E, such as the eye-refractive-power measuring system 100 shown in FIG. 3. The tonometry part 32 includes a configuration for measuring the ocular tension of the eye E, such as the tonometry system 200 shown in FIGS. 4 and 5. The tonometry part 32 according to the present embodiment is also capable of measuring the corneal thickness of the eye E. The respective parts of the measuring head 3 are controlled by the controller 60. The eye-refractive-power measuring part 31 and the tonometry part 32 are each equivalent to an example of the "examining part" of the present invention.

{Drive Mechanism}

The drive mechanism 10 has a vertical drive motor 14, an anteroposterior drive motor 17 and a horizontal drive motor 20, which are shown in FIG. 2. The controller 60 (drive controller 66) separately controls these motors 14, 17 and 20, thereby moving the measuring head 3 in the vertical direction, anteroposterior direction and horizontal direction, respectively.

{Calculator}

The calculator 40 calculates a predetermined measurement result based on information obtained by the measuring head 3. The eye-refractive-power calculator 41 calculates the sphericity, the degree of astigmatism, the astigmatic axis angle, etc., of the eye E based on the information obtained by the eye-refractive-power measuring part 31.

The ocular-tension calculator 42 calculates the value of ocular tension of the eye E based on the information obtained by the tonometry part 32. The corneal-thickness calculator 43 calculates the corneal thickness of the eye E based on the information obtained by the tonometry part 32. These calculation processes are executed as conventional.

{User Interface}

The user interface (UI) 50 includes a display device, an operation device, an input device, etc. To be specific, the user interface 50 includes a display 4, a control lever 5, a measurement switch 6, a jaw-rest moving switch 9, etc.

{Controller}

The controller 60 controls the respective parts of the opthalmologic apparatus 1. In particular, the controller 60 has a characteristic in control of the drive mechanism 10, i.e., control of movement of the measuring head 3. The controller 60 includes, for example, a microprocessor such as a CPU, a RAM, a ROM, a hard disk drive, a motor controller, etc. The controller 60 has a storage 61, an examination-completion detector 62, a head-position acquiring part 63, an examination-content specifying part 64, a movement-distance calculator 65, and a drive controller 66.

(Storage)

The storage 61 stores various kinds of information related to control of the opthalmologic apparatus 1. To be specific, the storage 61 stores information related to the control of the drive mechanism 10, such as retreat-distance information 61a. The storage 61 is equivalent to an example of the "storage" in the present invention.

The retreat-distance information 61a is information in which reference retreat distances corresponding to the respective examining parts of the measuring head 3 are registered. In this embodiment, reference retreat distances corresponding to the eye-refractive-power measuring part 31 and the tonometry part 32, respectively, are registered in the retreat-distance information 61a. A reference retreat distance is a retreat distance of an examination part, which is set in accordance with a working distance of the examining part without consideration of individual differences such as the height of the nose, the depth of the orbit and the height of the forehead.

Herein, in the opthalmologic apparatus 1 according to the present embodiment, when the eye E is changed from the left eye to the right eye or from the right eye to the left eye, the measuring head 3 is made to temporarily retreat before the change or simultaneously with the change in order to secure a certain safe distance from the eye E so as to prevent the patient from feeling fearful or anxious as a result of the movement of the machine in front of his/her eyes. That is, the retreat distance refers to a movement distance when the measuring head 3 (or the measuring pars 31 or 32) is moved backward (toward the operator) to a safe distance when the eye E is changed.

In order to secure a safe distance between the eye E and the measuring head 3, assuming the safe distance is constant, it is sufficient to make the measuring head retreat only by a difference obtained by subtracting a working distance from the safe distance. The working distance is a distance where the examining part and the eye E come into focus when the eye E is examined by the examining part, and is determined by lens arrangement of the optical system of the examining part. For example, a working distance Dr of the eye-refractive-power measuring part 31 (examination of the eye refractive power) and a working distance Dt of the tonometry part 32 (examination of ocular tension, examination of corneal thickness) are set to 50 mm and 11 mm, respectively.

Accordingly, the reference retreat distance may be represented as a distance equivalent to a difference obtained by subtracting, from a constant distance previously determined as a safe distance between the eye E and the measuring head 3, a working distance previously set for each examining part. The reference retreat distance becomes the shortest moving distance to secure safety. In the retreat-distance information 61a, values indicating the reference retreat distances are registered. A retreat distance may also be set with reference to a standard value of the height of the nose etc. (e.g., the result of measurement of a large number of subjects). That is, a retreat distance based on a reference retreat distance is the value of the reference retreat distance or a value obtained by correcting the reference retreat distance with reference to a standard value of the height of the nose, etc.

Furthermore, according to such a reference retreat distance, a difference in reference retreat distance between different examining parts is set to be equal to a difference in working distances therebetween, for example. To be specific, a difference between a reference retreat distance corresponding to the eye-refractive-power measuring part 31 and a reference retreat distance corresponding to the tonometry part 32 is set to be equal to a difference between the working distances of the measuring parts 31 and 32 (Dr−Dt=39 mm).

The working distance may be set as a distance between the tip position of the optical system installed in the examining part and the eye E, or may be set as a distance between the tip position of the examining part and the eye E. However, in this embodiment, it is assumed that a consistent definition of the working distance is used because the difference between working distances is taken into consideration with regard to each examining part.

(Examination-Completion Detector)

The examination-completion detector 62 detects that an examination by the eye-refractive-power measuring part 31 or tonometry part 32 is completed. To be specific, the examination-completion detector 62 detects that an examination immediately before the eye E is changed.

In an opthalmologic examination with the opthalmologic apparatus 1, a plurality of examinations are executed on the right and left eyes in accordance with a predetermined examination flow. As an example of the examination flow, examinations are executed in the following order: (1) measurement of eye refractive power of the right eye; (2) measurement of eye refractive power of the left eye; (3) measurement of ocular tension of the left eye (measurement of the corneal thickness); and (4) measurement of ocular tension of the right eye. In a case where this examination flow is applied, the examination-completion detector 62 detects that at least (1) and (3) are completed.

The eye refractive power examination is executed prior to the ocular tension examination because if the eye refractive power examination is executed after the shape of the cornea is deformed (applanated) in the ocular tension examination, there is a risk of causing an error in the examination results.

The examination-completion detector 62 detects, for example, completion of the examination based on the fact that the result of the examination is acquired. To be specific, the examination-completion detector 62 determines completion of the examination in response to the fact that execution of the examination, acquisition of the examination result and save of the examination result in the storage 61 are completed. If an examination flow is set to automatically execute a plurality of examinations with respect to the right and left eyes (i.e., if the step of "change of the eye" is previously included in the examination flow), it is not necessary to detect the completion of the examination and there is therefore no need to provide the examination-completion detector 62.

(Head-Position Acquiring Part)

The head-position acquiring part 63 acquires the position of the measuring head 3 at the current moment. If the eye-refractive-power measuring part 31 and the tonometry part 32 are independently movable, the head-position acquiring part 63 acquires the position of each of the measuring parts 31 and 32 at the current moment.

Furthermore, the head-position acquiring part 63 acquires, in particular, the vertical position of the measuring head 3 (refer to the explanation of the examination-content specifying part 64).

An example of the method for acquiring the position of the measuring head 3 will now be described. As a first example, there is a method of acquiring the position of the measuring head 3 based on the control content of the drive mechanism 10 by the drive controller 66.

The drive mechanism 10 operates in response to a control signal from the drive controller 66. That is, each of the drive motors 14, 17 and 20 (including the stepping motor) receives pulse signals from the drive controller 66 and moves the measuring head 3 by a distance corresponding to the number of pulses. A movement distance corresponding to one pulse is set in advance. Furthermore, it is assumed that, for example, at the time of start of an examination, the measuring head 3 is placed at a predetermined initial position.

According to this configuration, it is possible to acquire a three-dimensional position of the measuring head 3 at the current moment by referring to the historical record of control signals transmitted by the drive controller 66 from the state in which the measuring head 3 is placed at the initial position to the current moment. The initial position of the measuring head 3 may be set appropriately. For example, it is possible to set the initial position by the operation of the user, or may be set, after designation (input, selection, etc.) of a pupillary distance, a position corresponding to half the value of a pupillary distance as the initial position.

A second method is to actually detect the position of the measuring head 3. That is, it is a method of acquiring the position of the measuring head 3 by providing a sensor for detecting the position of the measuring head 3.

(Examination-Content Specifying Part)

The examination-content specifying part 64 specifies the content of an examination on the eye E. The content of an examination depend on the examining part disposed opposite to the eye E. As described before, the eye-refractive-power measuring part 31 and the tonometry part 32 are arranged next to each other in the vertical direction in the measuring head 3 of the present embodiment. The examination-content specifying part 64 specifies the examining part disposed opposite to the eye E based on the position of the measuring head 3 acquired by the head-position acquiring part 63, whereby the examination content is specified. If the eye-refractive-power measuring part 31 and the tonometry part 32 are arranged next to each other in the vertical direction, the vertical position of the measuring head 3 is sufficient for the position of the measuring head 3. The examination-content specifying part 64 composes an example of the "specifying part" of the present invention.

Moreover, it is also possible to specify the content of an examination based on the content of the examination having been determined as completed by the examination-completion detector 62.

Furthermore, if a flow of a plurality of examination is set in advance, the process of specifying the examination content is not required, and hence, there is no need to dispose the head-position acquiring part 63 and the examination-content specifying part 64.

(Movement-Distance Calculator)

The movement-distance calculator 65 calculates a horizontal distance between the examination position of a right eye and the examination position of a left eye. Herein, the examination position is a position for executing an examination on the eye E, i.e., a position of the examining part in a state in which alignment in each of the directions X, Y and Z is completed with respect to the eye E. The distance between the examining part placed at the examination position and the eye E is equivalent to the abovementioned working distance.

The movement-distance calculator 65 composes an example of the "calculator" of the present invention.

A specific example of a process executed by the movement-distance calculator 65 will now be described. Before the movement-distance calculator 65 operates, the head-position acquiring part 63 acquires the examination position in an examination of the right eye and the examination position in an examination of the left eye. At this moment, at least one examination position must be acquired with respect to each eye. When receiving the acquisition result by the head-position acquiring part 63, the movement-distance calculator 65 calculates the difference between the horizontal position indicated at the examination position of the right eye and the horizontal position at the examination position of the left eye. The calculation result (horizontal movement distance) is equivalent to a pupillary distance of the subject. Although the details will be described later, the horizontal movement distance is used when the measuring head 3 is moved next time.

(Drive Controller)

As previously described, the drive controller 66 controls the movement of the measuring head 3 by transmitting control signals (pulse signals) to the respective drive motors 14, 17 and 20.

[Operation]

Figure 7:
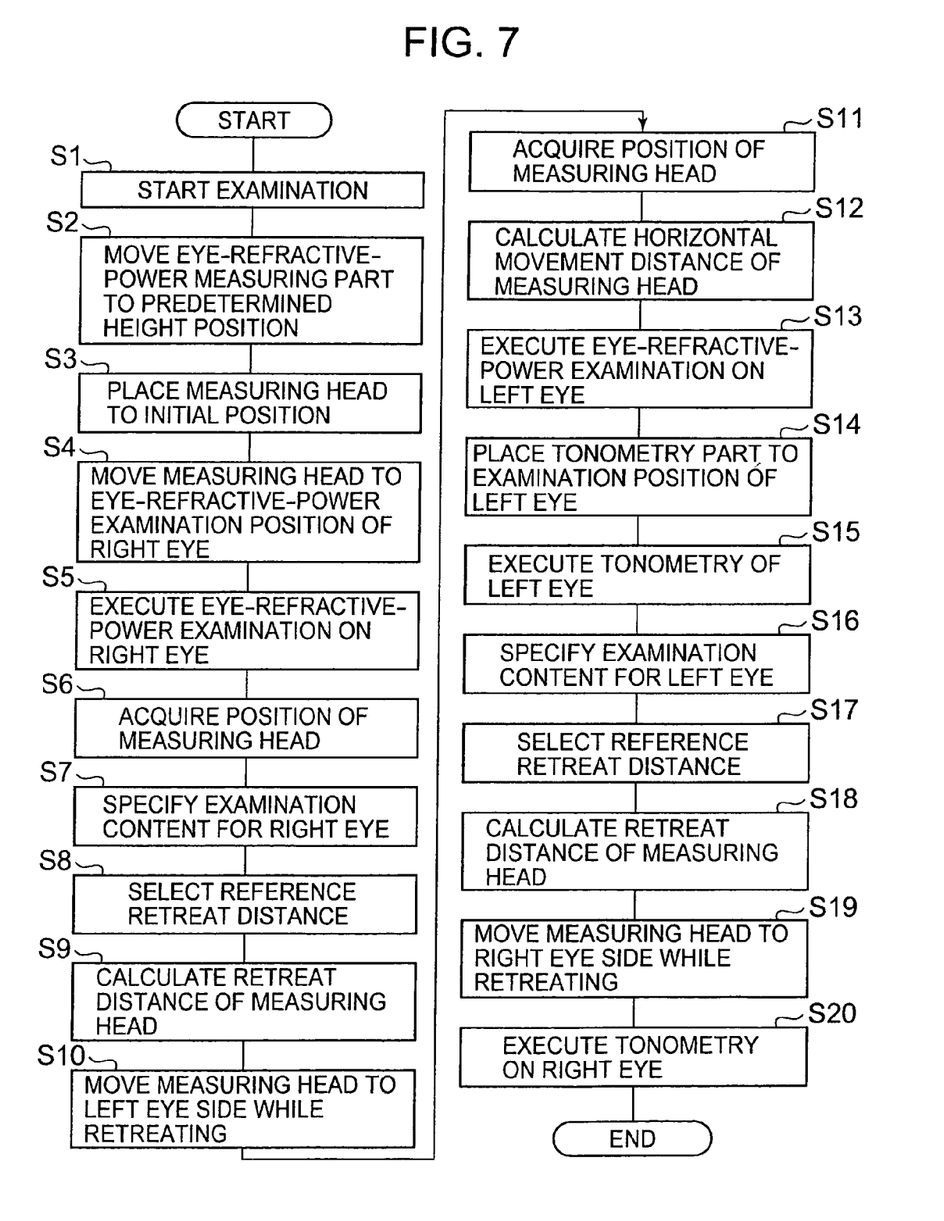
FIG. 7 shows an example of the operation of the opthalmologic apparatus according to the present embodiment.

The operation of the opthalmologic apparatus 1 will now be described. A flowchart in FIG. 7 shows an example of the operation of the opthalmologic apparatus 1.

First, an instruction to start an examination is given (S1). This instruction may be, for example, an operation of switching on the power supply of the opthalmologic apparatus 1, or may be an operation of designating a subject (such as a patient ID). Further, it is also possible to provide an operating part (hardware keys or software keys) for giving an instruction to start an examination. Moreover, data such as the height of the subject's nose may be inputted in this stage. When the instruction to start the examination is given, the drive controller 66 controls the drive mechanism 10 to move the measuring head 3 in the vertical direction, thereby moving the eye-refractive-power measuring part 31 to a predetermined height position (S2). The height position is equivalent to, for example, a standard height in the event of performing an eye refractive power examination, and is set in advance. The height position is used as, for example, the origin of the Y direction.

Next, the drive controller 66 controls the drive mechanism 10 to move the measuring head 3 in the horizontal direction, thereby placing the measuring head 3 at a predetermined initial position (S3). The initial position is a position equivalent to a previously set origin of each of the X and Y directions. This origin is, for example, set at a center position of the movable range in each of the X and Y directions.

Next, the measuring head 3 (eye-refractive-power measuring part 31) is moved to the examination position of the eye refractive power examination on the right eye of the subject (S4). This process is performed, for example, as described below.

As a first example, there is a method of automatically moving the measuring head 3. This method is, for example, to move the measuring head 3 only by a predetermined distance (for example, half a pupillary distance) in the right eye direction through the control by the drive controller 66 and execute alignment as conventional to place the eye-refractive-power measuring part 31 at an examination position for the right eye. The measuring head 3 may be moved until the right eye is detected by generating an image of the subject.

A second example is a method to semi-automatically move the measuring head 3. In this method, for example, the operator operates the control lever 5 to move the measuring head 3 to a position opposite to the right eye, and executes alignment as in the conventional method to place the eye-refractive-power measuring part 31 at an examination position for the right eye.

Next, the eye refractive power examination of the right eye is performed (S5). This process is executed by the eye-refractive-power measuring part 31 acquiring the data of the right eye and the eye-refractive-power calculator 41 by analyzing the data and calculating the eye refractive power of the right eye. The eye refractive power examination may be started automatically in response to the completion of the alignment, or it is also possible for the operator to manually start the same by, for instance, operating the measurement switch 6.

The examination-completion detector 62 detects the completion of the eye refractive power examination of the right eye.

The head-position acquiring part 63 acquires the position of the measuring head 3 at the time of execution of the eye refractive power examination on the right eye (S6). Furthermore, the examination-content specifying part 64 specifies the content of the examination executed on the right eye based on the position (particularly the vertical position) of the measuring head 3 (S7). The processes in Step 6 and 7 may be executed at any timing, e.g., before or after Step 5.

The drive controller 66 selects a reference retreat distance corresponding to the specified examination content (examining part) from the retreat-distance information 61a (S8), and calculates the retreat distance of the measuring head 3 based on the reference retreat distance (S9). At this moment, in calculation, it is possible to calculate the retreat distance in consideration of information such as the height of the subject's nose, etc. If the information such as the height of the subject's nose, etc. is not taken into consideration, the retreat distance indicated by the retreat-distance information 61a is acquired as it is.

Furthermore, the drive controller 66 controls the drive mechanism 10 to move the measuring head 3 to the left eye while making it retreat from the subject by the acquired or calculated retreating distance (S10).

Figure 8:
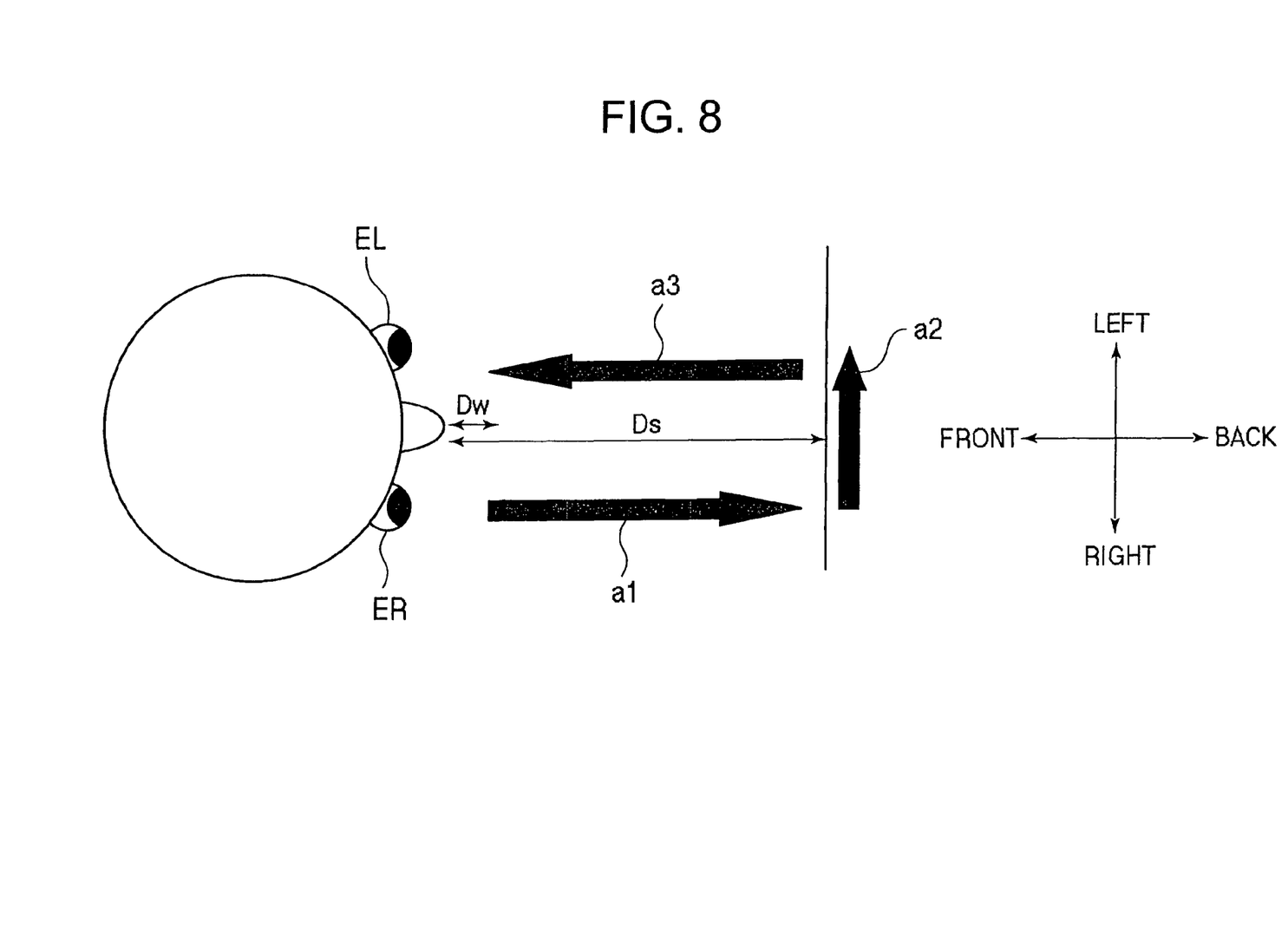
FIG. 8 shows an example of a first movement mode of a measuring head of the opthalmologic apparatus according to the present embodiment.
Figure 9:
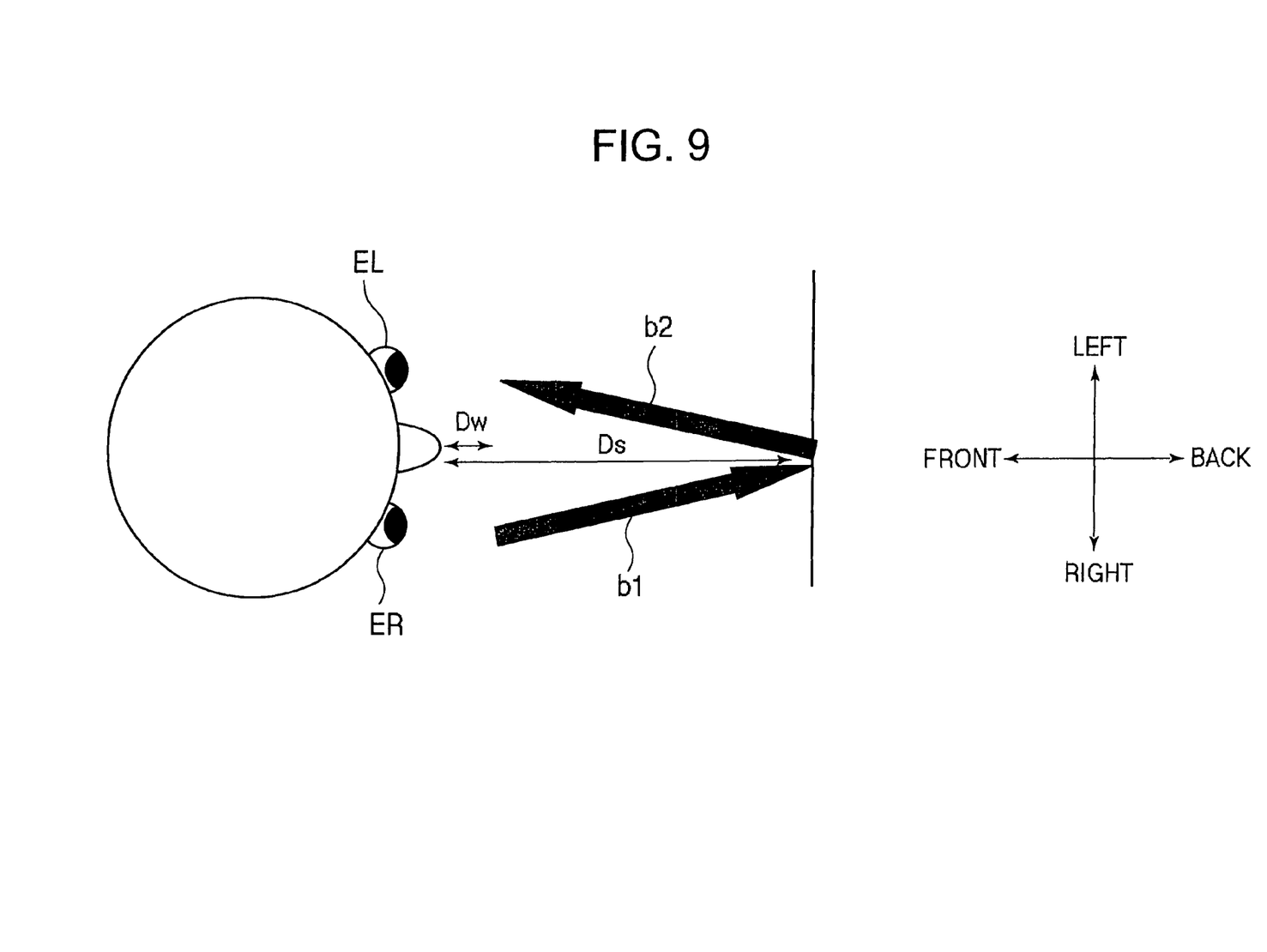
FIG. 9 shows an example of a second movement mode of the measuring head of the opthalmologic apparatus according to the present embodiment.
Figure 10:
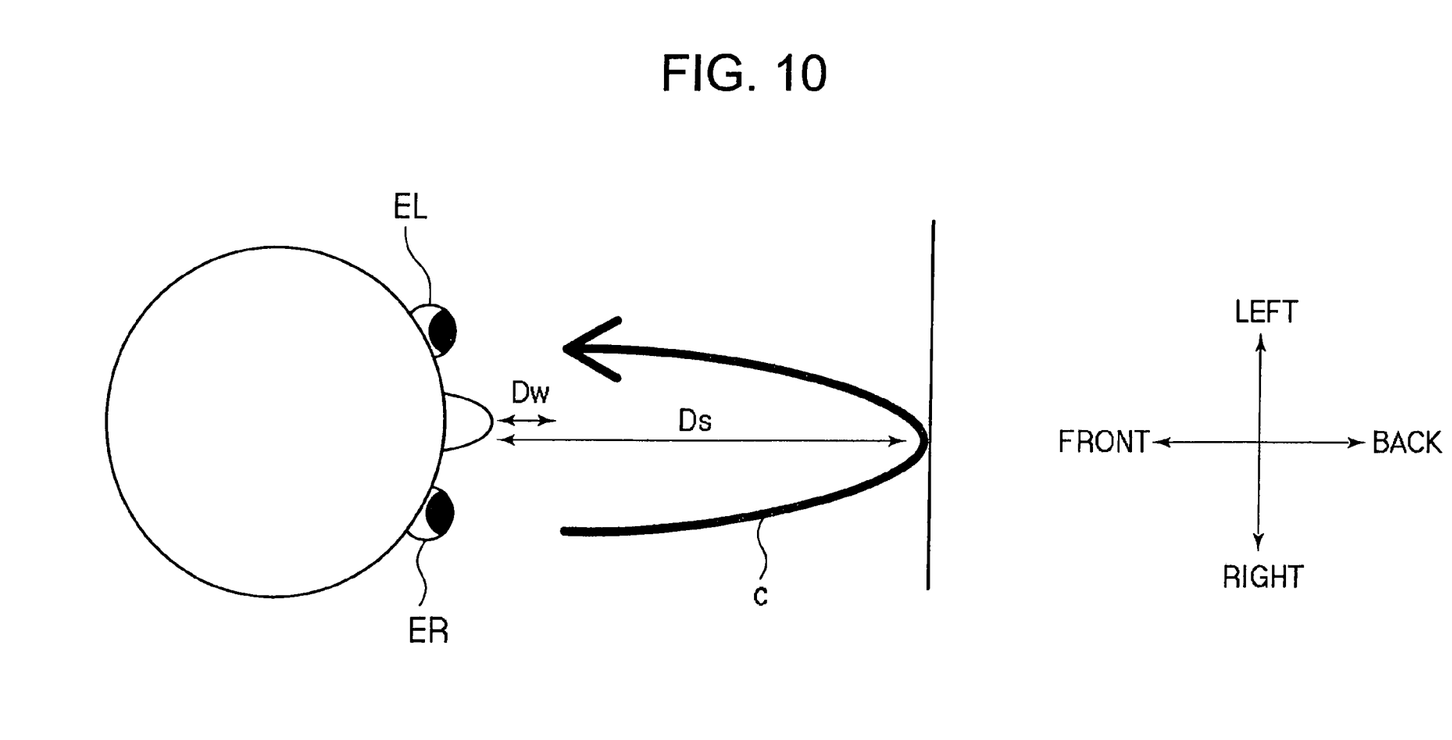
FIG. 10 shows an example of a third movement mode of the measuring head of the opthalmologic apparatus according to the present embodiment.

Examples of the mode at the time of moving the measuring head 3 from the right eye side to the left eye side are shown in FIGS. 8 to 10.

In the example shown in FIG. 8, first, the anteroposterior drive motor 17 is controlled to move the measuring head 3 positioned at an examination position for the right eye (trajectory a1), and the horizontal drive motor 20 is subsequently controlled to move the measuring head 3 to the left eye side in the left direction (trajectory a2), and next, the anteroposterior motor 17 is controlled to move the measuring head 3 to in front of the left eye in the frontward direction (trajectory a3).

Herein, the retreat distance along the trajectory a1 is equivalent to the calculated result in Step 9 and is either the difference obtained by subtracting a working distance Dw according to the specified content of the examination from a safe distance Ds, or a value calculated by incorporating the height of the subject's nose, etc. to the difference. The distance of the trajectory a2 is a distance indicated by the previous measurement results of the distance between the pupils of the patient. The distance is previously stored in the storage 61a by being linked to information indicating the subject, and the drive controller 66 reads out the same while causing the movement along the trajectory a2. The distance of the trajectory a2 may also be a standard value of the pupillary distance previously stored in the storage 61a.

Moreover, the movement along the trajectory a2 may also be a manual movement by the operator. After the movement along the trajectory a3, alignment with respect to the left eye is carried out as in the same conventional method to dispose the measuring head 3 at the examination position of the left eye.

In the example shown in FIG. 9, first, the anteroposterior drive motor 17 and the horizontal drive motor 20 are simultaneously controlled to linearly move the measuring head 3 positioned at the examination position of the right eye in the composite direction of the rearward direction and the leftward direction (in the rear-leftward direction) (trajectory b1), and next, the anteroposterior drive motor 17 and the horizontal drive motor 20 are simultaneously controlled to linearly move the measuring head 3 in the composite direction of the frontward direction and the leftward direction (in the front-leftward direction) up to the front of the left eye (trajectory b2).

Herein, the retreat distance at the time of the movement along the trajectory b1, i.e., the anteroposterior directional component of the trajectory b1 is equivalent to the calculated result in Step 9 and is a distance in accordance with the working distance Dw as in the case of FIG. 8. Furthermore, the horizontal directional component in the movement along each of trajectories b1 and b2 is set with, for example, a predetermined distance as in the case of FIG. 8. After the movement along the trajectory b2, the alignment is carried out to dispose the measuring head 3 at the examination position for the left eye.

In the example shown in FIG. 10, the anteroposterior drive motor 17 and the horizontal drive motor 20 are simultaneously controlled to move the measuring head 3 disposed at the examination position for the right eye to the front of the left eye along the arch-shaped trajectory shaped convexly on the rear side thereof. That is, in this example, the measuring head 3 is moved from the examination position of the right eye to the front of the left eye along the curved trajectory shaped convexly on the rear side thereof.

Here, a retreat distance at the time of movement along a trajectory c, i.e., a movement distance in the rearward direction is equivalent to the result of the calculation in Step 9, and is a distance in accordance with a working distance Dw as in FIG. 8. Further, a movement distance in the horizontal direction during the movement along the trajectory c is set to be, for example, a predetermined distance as in FIG. 8. After the movement along the trajectory c, the alignment is carried out to place the measuring head 3 at the examination position for the left eye.

When the measuring head 3 is placed at the examination position for the left eye, the head-position acquiring part 63 acquires the position of the measuring head 3 (S11). The movement-distance calculator 65 calculates the movement distance of the measuring head 3 in the horizontal direction, based on the positions acquired in Step 6 and Step 11, respectively (S12).

Next, as in Step 5, the eye-refractive-power examination is executed on the left eye (S13). When the eye-refractive-power examination on the left eye is completed, the drive controller 66 controls the vertical drive motor 14 to move the measuring head 3 in the vertical direction (the upward direction in this embodiment), thereby placing the tonometry part 32 in front of the left eye, and furthermore placing the tonometry part 32 at the examination position for the left eye by execution of the alignment as conventional (S14). At this moment, the drive controller 66 moves the measuring head 3 backward by a predetermined distance. This is because a working distance in the ocular tension examination is shorter than a working distance in the eye-refractive-power examination.

When the alignment is completed, the tonometry part 32 executes an ocular tension examination on the left eye (S15). This process is executed through acquisition of data of the left eye by the tonometry part 32 and analysis of the data and calculation of the ocular tension of the left eye by the ocular-tension calculator 42. Here, a corneal thickness examination may be executed as well as the ocular tension examination. Furthermore, the ocular tension examination may be automatically started in response to the completion of the alignment, or may be manually started through operation of the measurement switch 6 by the operator, for example. The examination-completion detector 62 detects the completion of the ocular tension examination on the left eye.

The examination-content specifying part 64 specifies the content of the examination (ocular tension examination) executed on the left eye based on the position (particularly, the position in the vertical direction) of the measuring head 3 acquired in Step 11 (S16). The drive controller 66 selects a reference retreat distance corresponding to the specified examination content from the retreat-distance information 61a (S17), and calculates the retreat distance of the measuring head 3 based on the reference retreat distance (S18). At this moment, it is possible to calculate the retreat distance in consideration of information such as the height of the patient's nose, etc, as well as the reference retreat distance.

Furthermore, the drive controller 66 controls the drive mechanism 10 to move the measuring head 3 toward the right eye while making the measuring head 3 retreat from the patient (S19). A retreat distance at this moment is equivalent to the result of the calculation in Step 18, and a rightward movement distance is equivalent to the result of calculation in Step 12. Moreover, as a movement mode at this moment, it is possible to apply those shown in FIGS. 8 to 10 as in Step 10.

When the alignment of the tonometry part 32 with respect to the right eye is completed, the ocular tension examination (and the corneal thickness examination) is executed on the right eye (S20). Then, the eye-refractive-power examination and the ocular tension examination on the right and left eyes by the opthalmologic apparatus 1 are completed.

[Actions and Effects]

As described above, the measuring head 3 of the opthalmologic apparatus 1 has a plurality of examining parts (the eye-refractive-power measuring part 31 and the tonometry part 32) that execute different examinations on the eye. The opthalmologic apparatus 1 is capable of three-dimensionally moving the measuring head 3. Thus, the opthalmologic apparatus 1 executes a plurality of examinations on each of the right and left eyes while changing the subject to be examined by the measuring head 3 from one eye to the other eye.

Furthermore, the opthalmologic apparatus 1 is configured to, when changing the eye to be examined, cause the measuring head 3 to retreat by a retreat distance in accordance with a working distance of the examining part positioned at the examination position for the one eye. Therefore, by causing the measuring head 3 to retreat by a distance in accordance with a working distance (a distance between the eye E and the examining part at the time of examination), the need for securing an unnecessarily long retreat distance is eliminated, and it is possible to reduce the examination time.

Further, since a retreating distance in accordance with a working distance is to be secured, it is possible to prevent the examining part from coming into contact with the subject, and it is possible to increase the safety.

Moreover, the opthalmologic apparatus 1 previously stores the retreat-distance information 61a in which the reference retreat distances corresponding to the respective examining parts are registered, and causes the measuring head 3 to retreat by selectively referring to the reference retreat distance corresponding to the examining part positioned at the examination position of the one eye.

Consequently, it is possible to easily and securely apply the retreat distance corresponding to the examining part. Furthermore, the opthalmologic apparatus 1 is capable of obtaining a retreat distance with reference to, as well as the reference retreat distance, individual data such as the height of the subject's nose, etc, and therefore it is favorable in both reduction of an examination time and secure of safety.

Moreover, according to the present embodiment, it is possible to set a difference in retreat distance between the different examining parts to be equal to a difference in working distance therebetween, and therefore, the need for causing the measuring head 3 to retreat by an unnecessarily long distance when switching the right and left eyes is eliminated, whereby it becomes possible to reduce the examination time.

Furthermore, according to the opthalmologic apparatus 1, it is possible to move the measuring head 3 along various trajectories as shown in FIGS. 8 to 10. A favorable retreat distance may be realized by applying any trajectory. In particular, by reducing the movement distance by applying the trajectory shown in FIG. 9 or FIG. 10, it is possible to reduce the switching time between the right and left eyes. It is also possible to employ any other trajectory other than the above as necessary. For example, it is possible to change the examination target from one eye to the other eye by firstly moving the measuring head 3 diagonally backward, subsequently moving in the horizontal direction, and further moving diagonally forward.

Furthermore, according to the opthalmologic apparatus 1, it is possible to calculate a horizontal distance between the examination positions for both the eyes. This distance is approximation of the pupillary distance of the subject. The opthalmologic apparatus 1 is configured to, at the time of switch between the right and left eyes again, move the measuring head 3 in the horizontal direction by the distance obtained by the above calculation. Consequently, it is possible to favorably obtain the horizontal movement distance of the measuring head 3 in the examinations of the right and left eyes. In particular, reduction of a time for switch between the right and left eyes makes shift of the position of the eye during the switch less possible, and thus, it is possible to obtain the pupillary distance with higher accuracy than conventional. Consequently, it becomes possible to reduce the alignment time, and moreover, reduce the examination time.

Moreover, according to the opthalmologic apparatus 1, it is possible to automatically start the switch between the right and left eyes in response to detection of completion of an examination.

Consequently, it is possible to further reduce the examination time.

[Modification]

The above detailed description is merely an example of the configuration and operation for favorably implementing the present invention. Therefore, it is possible to appropriately modify within the scope of the present invention. For example, in the above embodiment, an opthalmologic apparatus having two examining parts is described, but any number of the examining parts maybe installed in the opthalmologic apparatus according to the present invention.

Furthermore, in the above embodiment, the switch between the right and left eyes (Steps 10, 19) and the switch of the examining parts (Step 14) are conducted at different timings, but it is also possible to execute these two switching operations together. In this case, either of the operations may be conducted first. In addition, it is also possible to execute both operations at the same time.

Moreover, in the above embodiment, there is no mention of the moving speed of the measuring head 3, but the moving speed may be thought out. For example, it is possible to control so that a speed when the measuring head 3 is moved backward is faster than a speed when moved in the forward direction. That is, it is possible to control to cause the measuring head 3 to retreat at a relatively high speed and advance at a relatively low speed. It is thereby possible to further reduce the moving time and further increase the safety.

What is claimed is:

1. An ophthalmologic apparatus, comprising:
   an examination unit including a plurality of examining parts executing different examinations on an eye;
   a driver configured to move the examination unit in a horizontal direction and an anteroposterior direction;
   a storage configured to previously store retreat-distance information in which a reference retreat distance for each of the plurality of examining parts is registered; and
   a controller configured to, when an examination subject by the examination unit is switched from one eye to the other eye, select a reference retreat distance related to an examining part located at the examination position for the one eye, and control the driver to make the examination unit retreat by a retreat distance based on the selected reference retreat distance in the anteroposterior direction away from the eye, wherein:
   a first examining part and a second examining part have different working distances and have different retreat distances of the plurality of the examining parts, and wherein a difference between a retreat distance corresponding to the first examining part and a retreat distance corresponding to the second examining part is equal to a difference between a working distance of the first examining part and a working distance of the second examining part.

2. An ophthalmologic apparatus, comprising:
   an examination unit in which a plurality of examining parts configured to execute different examinations on an eye are included next to each other in a vertical direction;
   a driver configured to move the examination unit in anteroposterior, horizontal and vertical directions;
   a specifying part configured to specify an examining part located at an examination position for one eye based on a vertical position of the examination unit;
   a storage configured to previously store retreat-distance information in which a reference retreat distance is registered for each of the plurality of examining parts; and
   a controller configured to control the driver to, when an examination subject by the examination unit is switched from the one eye to the other eye, select a reference retreat distance related to the examining part specified by the specifying part from the retreat-distance information, and to cause the examination unit to retreat by the reference retreat distance based on the selected reference retreat distance in the anteroposterior direction away from the eye, wherein:
   a first examining part and a second examining part have different working distances and have different retreat distances of the plurality of the examining parts, and wherein a difference between a retreat distance corresponding to the first examining part and a retreat distance corresponding to the second examining part is equal to a difference between a working distance of the first examining part and a working distance of the second examining part.

3. The ophthalmologic apparatus according to claim 1, wherein:
   the controller controls the driver to make the examination unit retreat by a retreat distance equivalent to a difference between a constant distance previously determined from the eye to the examining part to be secured when the examination target is switched from one eye to the other eye and the working distance.

4. The ophthalmologic apparatus according to claim 1, wherein:
   the plurality of examining parts are arranged next to each other in a vertical direction;
   the driver moves the examination unit in the vertical direction; and
   the controller includes a specifying part configured to specify an examining part located at the examination position of the one eye based on a vertical position of the examination unit.

5. The ophthalmologic apparatus according to claim 1, wherein:
   the controller controls the driver to cause the examination unit to retreat along the anteroposterior direction from the examination position of the one eye by the retreat distance, subsequently move it along the horizontal direction toward the other eye, and subsequently move it along the anteroposterior direction toward an examination position of the other eye.

6. The ophthalmologic apparatus according to claim 1, wherein:
   the controller controls the driver to linearly move the examination unit along a composite direction of a direction of the other eye and a backward direction from the examination position of the one eye, and to further linearly move it along a composite direction of the direction of the other eye and a forward direction toward an examination position of the other eye.

7. The ophthalmologic apparatus according to claim 1, wherein:
   the controller controls the driver to move the examination unit along an arch-shaped trajectory convexed backward from the examination position of the one eye toward an examination position of the other eye.

8. The ophthalmologic apparatus according to claim 1, wherein:
   the controller includes a calculator configured to calculate a horizontal distance between the examination position of the one eye and an examination position of the other eye; and
   the controller controls the driver to, when the examination target by the examination unit is switched again, move the examination unit in the horizontal direction by a distance previously calculated by the calculator.

* * * * *